United States Patent
Kamahori et al.

(10) Patent No.: US 8,394,247 B2
(45) Date of Patent: Mar. 12, 2013

(54) ANION CONCENTRATION MEASURING DEVICE AND ANION CONCENTRATION MEASURING ELEMENT

(75) Inventors: Masao Kamahori, Kokubunji (JP); Yu Ishige, Tokyo (JP); Kotaro Yamashita, Mito (JP); Yasuhisa Shibata, Hitachiomiya (JP); Masafumi Miyake, Hitachinaka (JP); Kuniaki Nagamine, Hachioji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1011 days.

(21) Appl. No.: 12/222,900

(22) Filed: Aug. 19, 2008

(65) Prior Publication Data

US 2009/0071826 A1  Mar. 19, 2009

(30) Foreign Application Priority Data

Sep. 19, 2007 (JP) ................. 2007-242790
Jun. 6, 2008 (JP) ................. 2008-149385

(51) Int. Cl.
*G01N 27/333* (2006.01)

(52) U.S. Cl. ............ 204/416; 205/789; 257/253

(58) Field of Classification Search .......... 204/418, 204/403.01–403.15, 419; 257/253; 435/6; 205/777.5, 778, 792, 789
See application file for complete search history.

(56) References Cited

U.S. PATENT DOCUMENTS 5,116,481 A * 5/1992 Ozawa et al. ........... 204/403.06
2006/0016699 A1   1/2006 Kamahori et al.
2009/0071826 A1 * 3/2009 Kamahori et al. ........ 204/418

FOREIGN PATENT DOCUMENTS

EP  0 300 364 A2   1/1989
EP  1619496 A1 *   1/2006

(Continued)

OTHER PUBLICATIONS

Flink, Simon, Bernard A. Boukamp, Albert Van Den Berg, Frank C. J. M. Van Veggel, and David N. Reinhoudt. "Electrochemical Detection of Electrochemically Inactive Cations by Self-Assembled Monolayers of Crown Ethers." Journal of the American Chemical Society 120.19 (1998): 4652-657.*

(Continued)

*Primary Examiner* — Kaj K Olsen
*Assistant Examiner* — Kourtney R Carlson
(74) *Attorney, Agent, or Firm* — Stites & Harbison, PLLC; Juan Carlos A. Marquez, Esq.; Stephen J. Weyer, Esq.

(57) ABSTRACT

The present invention aims to simplify the structure and a fabrication method of an ion-selective electrode in an ion concentration measuring device that measures an anion, particularly a chloride ion, in a biological component. To this end, in a potential difference measuring unit, a quaternary ammonium salt derivative serving as a ligand for an anion is immobilized to the surface of a gold electrode by using as a linker an insulative molecule forming a self-assembled monolayer. The potential difference measuring unit measures an electromotive force generated with anion binding, as an interface potential change on the surface of the gold electrode. In order to reduce the influence of adsorption of impurities on the electrode surface, a high-molecular weight polymer is physically adsorbed on the gold electrode and thus used when a biological component is measured.

5 Claims, 11 Drawing Sheets

FOREIGN PATENT DOCUMENTS

| | | |
|---|---|---|
| JP | 61-170645 | 1/1985 |
| JP | 03-259739 A | 11/1991 |
| JP | 2004-184365 | 12/2002 |
| JP | 2005-265727 | 9/2005 |
| JP | 2006-30132 A | 2/2006 |
| WO | WO 2006/113440 A2 | 4/2006 |

OTHER PUBLICATIONS

English translation of the Japanese Office Action dated May 8, 2012.*

Flink, Simon, et al., "Electrochemical Detection of Electrochemically Inactive Cations by Self-Assembled Monolayers of Crown Ethers", Journal of American Chemical Society, vol. 120, No. 19, 1998, pp. 4652-4657.

Wanichacheva, Nantanit, et al., "Surface-Based Lithium Ion Sensor: An Electrode Derivatized with a Self-Assembled Monolayer", Analytical Chemistry, vol. 78, No. 20, Oct. 15, 2006, pp. 7132-7137.

Zhang, Sheng, et al., "Selective Anion Sensing Based on Tetra-amide Calix[6]arene Derivatives in Solution and Immobilized on Gold Surfaces via Self-Assembled Monolayers", Langmuir, vol. 22, No. 25, 2006, pp. 10732-10738.

Office Action, from Japan Patent Office, issued in corresponding Japanese Patent Application No. 2008-149385, dated May 8, 2012, pp. 1-3.

European Search Report from the European Patent Office, issued in corresponding European Patent Application No. 08014646.7, dated Nov. 29, 2012, pp. 1-4.

W. Knoll et al., "Supramolecular Engineering at Functionalized Surfaces," Synthetic Metals, Elsevier Sequoia, vol. 61, Nov. 23, 1993, pp. 5-11.

S. Flink et al., "Sensor Functionalities in Self-Assembled Monolayers," Advanced Materials, vol. 12, No. 18, Sep. 15, 2000, pp. 9-15.

* cited by examiner

ANION CONCENTRATION MEASURING DEVICE AND ANION CONCENTRATION MEASURING ELEMENT

CLAIM OF PRIORITY

The present application claims priority from Japanese patent applications JP 2007-242790 filed on Sep. 19, 2007 and JP 2008-149385 filed on Jun. 6, 2008, the contents of which are hereby incorporated by reference into this application.

BACKGROUND OF THE INVENTION

1. Field of the Invention

The present invention relates to an anion concentration measuring device to measure anions, particularly chloride ions, in a biological component.

2. Description of the Related Art

Ion-selective electrode techniques are widely used as methods of analyzing the concentrations of biological substances in the medical field, particularly, electrolytes (sodium ions, potassium ions, and chloride ions, and the like) in serums and plasmas. In the ion-selective electrode techniques, the ion concentration in a sample can be measured by simply immersing an ion-selective electrode together with a reference electrode in the sample solution. Thus, the ion-selective electrode techniques are employed in automatic biochemical analyzers to make use of their advantages of achieving the miniaturization and automation of the analyzers.

Among the ion-selective electrodes, chloride ion-selective electrodes are classified into: a solid-state electrode made of a hardly-soluble chloride; and a liquid-membrane electrode to which an ion-exchange type ligand is added. A conventional liquid-membrane chloride-ion-selective electrode is formed in a way that a plastic film made of an epoxy resin and vinyl chloride is added with a plasticizer (e.g., dialkyladipate or dialkylphthalate) and a quaternary ammonium salt as a ligand. The quaternary ammonium salt used as the ligand is any of trioctylmethylammonium chloride, tridecylmethylammonium chloride and tetraoctylammonium chloride, for example. In addition, to enhance the improvement of the physical strength and the selectivity for chloride ions, there has been developed a chloride ion-selective electrode made of a copolymer of: a styrene monomer having a tri-long-chain alkylammonium group that is a ligand as a side chain; and a polymer having a hydrophilic group as a side chain (Japanese Patent Application Publication No. 2004-184365). On the other hand, to improve the physical strength and to prevent the elution of the ligand from deteriorating an electrode, there has also been developed an ion-selective electrode of a chemically modified glass film that uses, as a sensitive membrane, a porous glass to which a quaternary ammonium salt as a ligand is immobilized (Japanese Patent Application Publication No. Sho 61(1986)-170645).

An ion-selective electrode that includes a ligand immobilized on the surface of a gold electrode has been proposed in order to simplify the structure and the fabrication method of the above-mentioned ion-selective electrode and to achieve the miniaturization of analysis equipment in the future. Any of these ion-selective electrodes, however, is not capable of measuring an electric potential, and an ion concentration to be measured is obtained by impedance measurement. An example of a sodium ion-selective electrode has been reported in which a mercapto-crownether compound as a neutral-carrier type ligand is immobilized to a gold electrode (J. Am. Chem. Soc., 120 (1998) 4652-4657). In addition, examples of a lithium ion-selective electrode include an electrode in which a neutral-carrier type ligand is similarly immobilized to the surface of a metal electrode by utilization of bonding between thiol residue and gold (Anal. Chem., 78 (2006) 7132-7137, and WO2006/113440). Moreover, as anion selective electrodes, there has been an electrode in which a ligand for a fluoride ion (tetra-amide Calix [6] arene derivative) is immobilized on the surface of a gold electrode by utilization of bonding between thiol residue and gold (Langmuir, 2006, 22, 10732-10738).

SUMMARY OF THE INVENTION

The ion-selective electrode in which the above-mentioned ligand is immobilized to the gold electrode surface cannot measure a potential because the electrode is configured without the consideration of the insulation of the gold electrode surface and the surrounding environments of the ligand. Because of this, an ion concentration to be measured is obtained by use of impedance measurement. More specifically, the conventional ligand-immobilized ion-selective electrodes are configured without taking account of the insulation between a measurement solution and the gold electrode surface to which the ligand is immobilized. Accordingly, in an actual measurement, the conventional ligand-immobilized ion-selective electrodes cannot stably measure the interface potential due to an adverse influence of a leak current from a space between immobilized ligands. In the impedance measuring technique, the potential is measured by placing, in a solution, a working electrode and a counter electrode made of gold or platinum, as well as a reference electrode for keeping the potential of the reference electrode constant, and then by measuring a current value of a frequency response to a voltage applied between the working electrode and the counter electrode with use of a potentiostat that is a current measuring device. At this time, a redox material that is an electrochemical activator needs to be placed in the measurement solution. Thus, although the conventional ion-selective electrode techniques have the advantage that the concentration of an ion in a sample can be measured by simply immersing an ion-selective electrode in a sample solution together with a reference electrode, such advantage is not utilized at all. Moreover, the impedance measuring technique is a current measuring method, and thus principally poses a problem that the concentration measurement range is narrow.

An object of the present invention is to provide an ion concentration measuring device including an ion-selective electrode with a simple structure that is capable of measuring an ion concentration in a sample by simply immersing an ion-selective electrode together with a reference electrode in a sample solution, while maintaining an advantage and basic performances such as a measurement concentration range of conventional liquid-membrane ion-selective electrode methods and. to provide a fabrication method of the ion-selective electrode.

To achieve the above-mentioned object, in the present invention, a quaternary ammonium salt derivative serving as a ligand for an anion is immobilized to the surface of a gold electrode using as a linker an insulative molecule (e.g., an alkanethiol) forming a self-assembled monolayer. Then, an electromotive force generated with coordination of an anion is measured as an interface potential change on the surface of the gold electrode. At the time, in a case where an alkyl group at the side chain of the quaternary ammonium salt derivative is larger than the interval of the self-assembled monolayer and where there is a space between immobilized ligand molecules, an alkanethiol which has a carbon chain shorter than the linker and includes one hydrophilic terminal is immobilized to the surface of the gold electrode to coexist with the quaternary ammonium salt derivative. The alkanethiol herein has a hydrophilic group at the hydrophilic terminal, for example, of an amino group or a hydroxyl group. The number of carbon atoms of the linker is desirably from 6 to 20 inclusive in order to efficiently form the self-assembled monolayer. In addition, it is desirable that the number of carbon atoms of the alkyl chain at each of the other three side chains of the quaternary ammonium salt be smaller than the number of carbon atoms of the linker so as not to hinder the self-assembled monolayer formation. Additionally, an insulated gate field-effect transistor formed on the same substrate as that of the gold electrode is used as a potentiometer. In that case, an alternating voltage of 1 KHz or more is superimposed on a reference electrode, and the measurement is carried out. Moreover, in order to reduce the influence of adsorption of impurities, a high-molecular weight polymer is physically adsorbed on the gold electrode and thus used when a biological component is measured.

According to the present invention, the insulation between the gold electrode and a solution can be improved in a way that the quaternary ammonium salt derivative serving as the ligand for an anion is immobilized to the surface of the gold electrode by using the insulative molecule. The improvement of this insulation can restrain a leak current from a space between the ligands, and makes it possible to stably measure an electromotive force generated by the coordination of an anion, as an interface potential change of the gold electrode surface. When an alkyl group at the side chain of the quaternary ammonium salt derivative is larger than the interval of the self-assembled monolayer, an alkanethiol which has a carbon chain shorter than the linker and includes one hydrophilic terminal is immobilized to the surface of the gold electrode to coexist with a quaternary ammonium salt derivative. Thereby, the space between the immobilized ligand molecules is eliminated, and the insulation between the gold electrode and the solution is maintained. In that case, if an alkanethiol having an amino group at the hydrophilic terminal as the alkanethiol including the hydrophilic terminal, a response speed is effectively increased. In addition, the insulated gate field-effect transistor formed on the same substrate as that of the gold electrode is used as the potentiometer. The use of the insulated gate field-effect transistor leads to a decrease in the leak current, and a stable measurement of the interface potential of the gold electrode surface. In that case, by superimposing an alternating voltage of 1 KHz or more on the reference electrode, the interface potential of the gold electrode surface is stabilized, and the measurement precision is improved. Additionally, a high-molecular weight polymer is physically adsorbed on the gold electrode and used to reduce a noise and a drift due to the adsorption of impurities on the electrode surface during a biological component measurement.

BRIEF DESCRIPTION OF THE DRAWINGS

FIG. 2 is a diagram indicating an example in which a ligand for a chloride ion is immobilized to a gold electrode.

FIG. 4 is a diagram indicating a structural example of an analysis element with an FET sensor used for the ion concentration measuring device of the present invention.

FIG. 5 is a diagram indicating influences of the length of a carbon chain and a terminal residue of an alkanethiol that is made to coexist with a ligand, on a response speed to a chloride ion concentration.

DESCRIPTION OF THE PREFERRED EMBODIMENTS

Embodiments of the present invention will be described with reference to the drawings, hereinafter.

Figure 1:
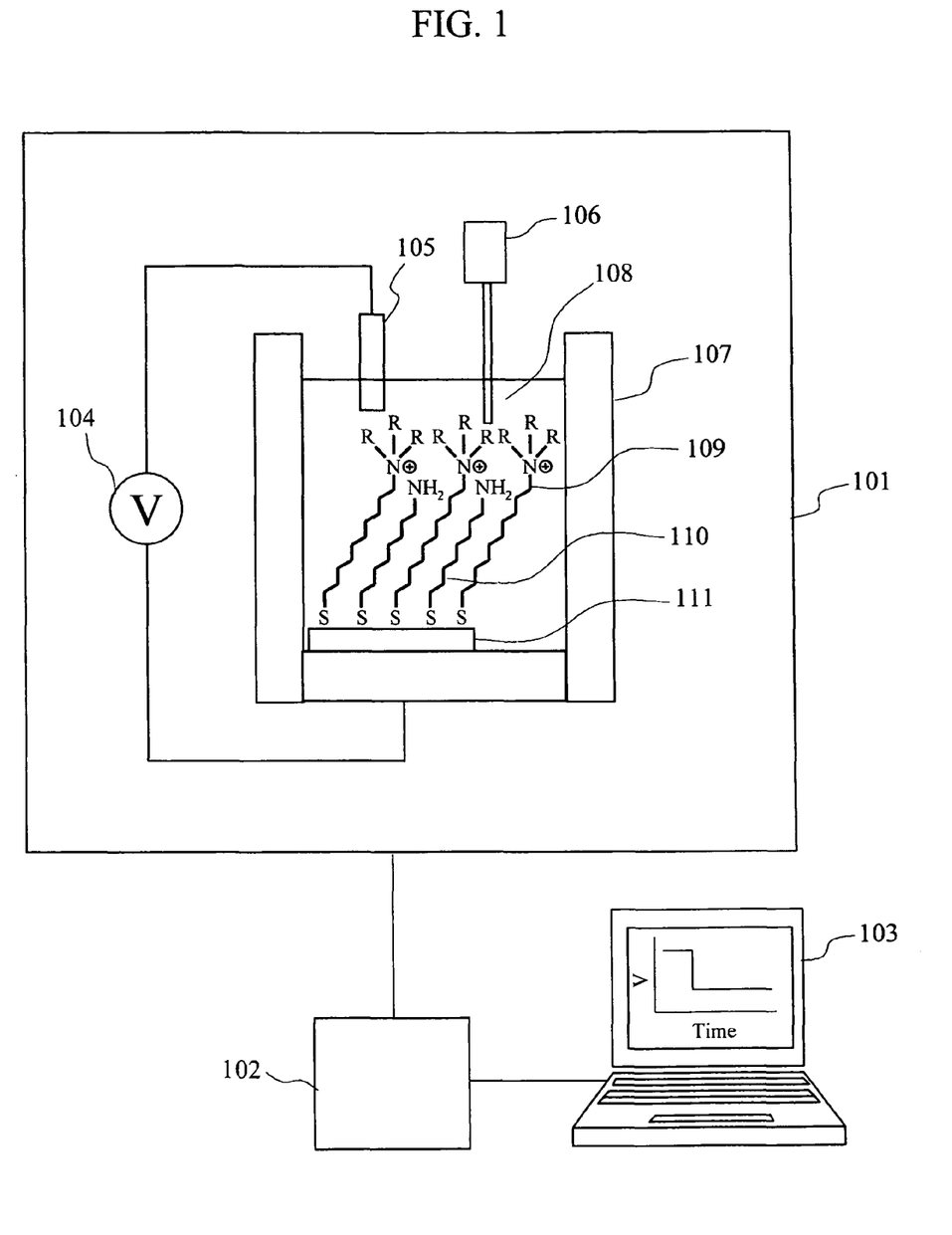
FIG. 1 is a block diagram indicating one example of an ion concentration measuring device according to the present invention.
Figure 2A:
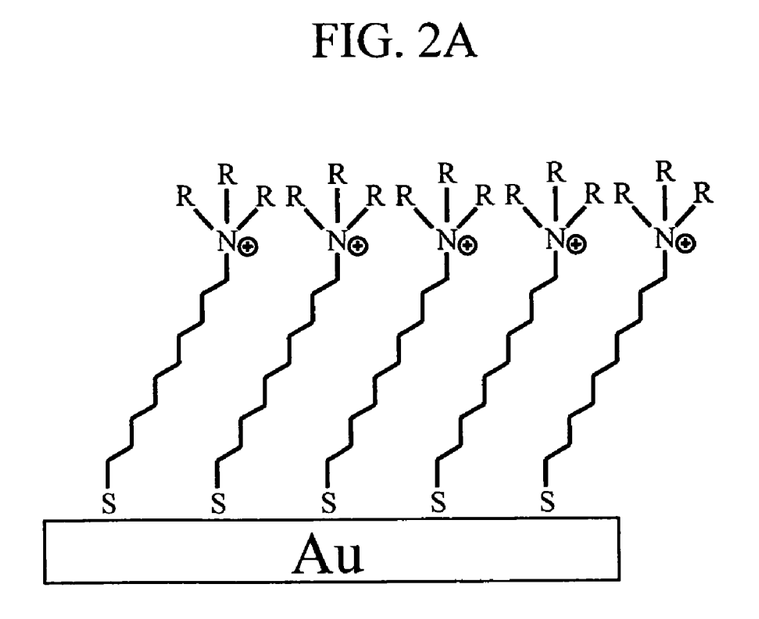
FIG. 2A show a case where only a quaternary ammonium salt derivative serving as the ligand for a chloride ion is immobilized.
Figure 2B:
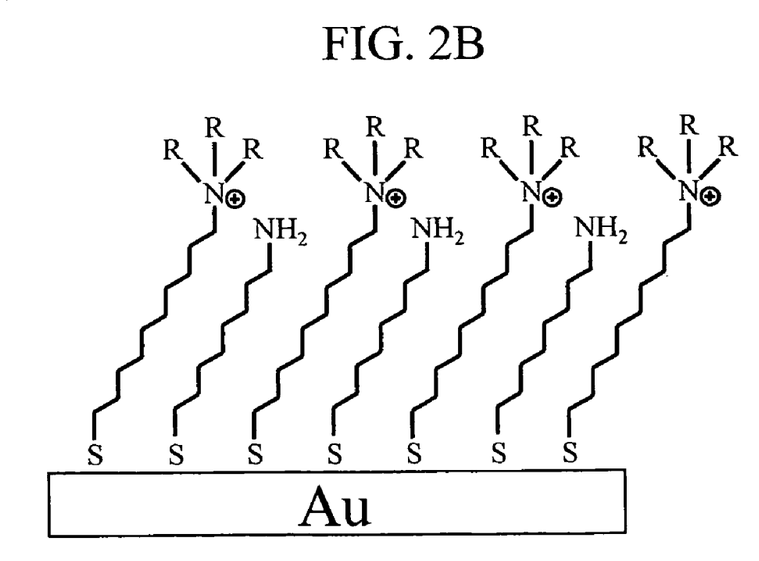
FIG. 2B shows a case where a quaternary ammonium salt derivative serving as the ligand for a chloride ion and an alkanethiol having an amino group at its terminal are immobilized to coexist with each other.

FIG. 1 is a block diagram indicating one example of an ion concentration measuring device according to the present invention. The measuring device in this embodiment includes a measurement section 101, a signal processing circuit 102, and a data processor 103. The measurement part 101 includes a potentiometer 104, a reference electrode 105, a sample solution injector 106 that supplies a sample solution having an analyte, and a measurement cell 107. The reference electrode 105A and a gold electrode 111 to which a quaternary ammonium salt derivative 109 serving as a ligand for an anion and an alkanethiol 110 having an amino group at its terminal are immobilized, are arranged in a measurement solution 108 in the measurement cell 107. FIG. 2 shows one example of an immobilization method of a ligand to a gold electrode. FIG. 2A shows a case where only a ligand is immobilized; and FIG. 2B shows a case where a ligand and an alkanethiol having an amino group at its terminal are immobilized while coexisting. The ligand for a chloride ion is N,N,N-trimethyl(10-mercaptodecyl)ammonium chloride, and the alkanethiol having an amino group at its terminal is 8-amino-1-octanethiol. In addition, carbon chains of an alkyl group at a side chain of the quaternary ammonium salt derivative serving as the ligand for a chloride ion can be altered, depending on measurement conditions. In that case, the number of carbon atoms of the alkyl group at the side chain of the quaternary ammonium salt derivative is desirably smaller than the number of carbons of a linker so as not to prevent self assembly when the ligand is immobilized to the gold electrode. In addition, the length of the carbon chain of an alkanethiol that is made to coexist at this time poses no problems so long as it is the length of the carbon chain of the linker for the quaternary ammonium salt derivative or shorter. For instance, when the number of carbons of the carbon chain of the linker for the quaternary ammonium salt derivative is 10,6-amino-1-hexanethiol, 8-amino-1-octanethiol and 11-amino-1-undecanthiol, each of which has an amino group at its terminal, as well as 6-hydroxy-1-hexanethiol, 8-hydroxy-1-octanethiol and 11-hydroxy-1-undecanethiol, each of which has an hydroxyl group at its terminal, can also be used.

The measurement procedure is as follows. First, a sample solution is injected into the measurement solution 108 within the measurement cell 107 by means of the sample solution injector 106. A chloride ion that is a target for measurement in the sample solution is bonded to the quaternary ammonium salt derivative 109 serving as the ligand for an anion by ion exchange action, so that the interface potential on the gold electrode 111 is changed. In the potential measurement, the interface potential of the gold electrode 111 that is changed prior to and after the sample solution injection with the sample solution injector 106, is measured in real time by means of the potentiometer 104, and then recorded by use of the signal processing circuit 102 and the data processor 103. The interface potential change on the gold electrode 111 depends on the concentration of the chloride ion that is the target for measurement. Therefore, on the basis of a calibration curve constructed in advance by measuring standard solutions, an unknown chloride ion concentration of the sample can be obtained from the measured potential change value.

The sample solution injector 106 can utilize a syringe pump or a pressurizing-type solution sending device. In addition, in place of the gold electrode 111, an electrode made of carbon or another noble metal such as silver may be used. Additionally, a high-molecular weight polymer may be physically adsorbed on the gold electrode and used to reduce an influence of adsorption of impurities on the electrode surface when a biological component is measured. The high-molecular weight polymer that may be used includes methyl cellulose, acrylamide, dextran, polyethylene glycol, and the like.

The reference electrode 105 gives a reference potential in order to stably measure a potential change on the basis of an equilibration reaction or a chemical reaction taking place on the surface of the gold electrode 111 within the measurement solution 108. Normally, a calomel electrode or a silver/silver chloride electrode in which a saturated potassium chloride solution is used as an internal solution is used as the reference electrode. However, when the composition of a sample solution to be measured is uniform, only a silver/silver chloride electrode can be used as a pseudo-electrode without problems.

Figure 3:
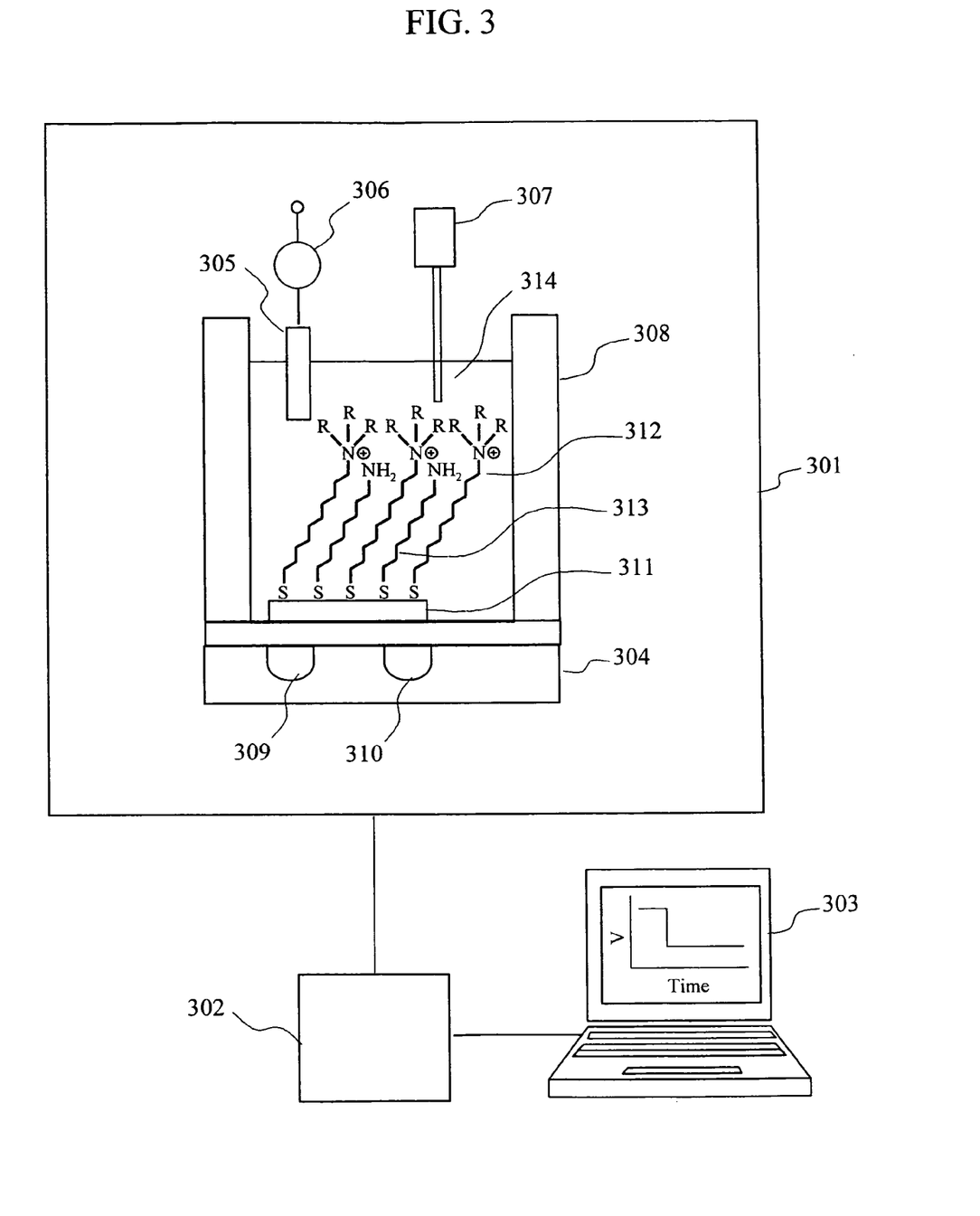
FIG. 3 is a block diagram indicating one example of an ion concentration measuring device using an FET sensor according to the present invention.

FIG. 3 is a block diagram indicating one example of an ion concentration measuring device using a field-effect transistor (FET) sensor according to the present invention. The measuring device of this embodiment includes a measurement section 301, a signal processing circuit 302 and a data processor 303. The measurement section 301 includes an insulated gate field-effect transistor 304, a reference electrode 305, a power source 306 that applies a voltage to the reference electrode 305, a sample solution injector 307 that supplies a sample solution having an analyte, and a measurement cell 308. The insulated gate field-effect transistor 304 includes a source 309, a drain 310 and a gold electrode 311 that is electrically connected to a gate. A quaternary ammonium salt derivative 312 serving as a ligand for an anion and an alkanethiol 313 having an amino group at its terminal are immobilized to the gold electrode 311. The reference electrode 305 and the gold electrode 311 to which a quaternary ammonium salt derivative 312 serving as the ligand for an anion and the alkanethiol 313 are immobilized, are arranged in the measurement solution 314 in the measurement cell 308.

The measurement procedure is as follows. First, a sample solution is injected into the measurement solution 314 within the measurement cell 308 by means of the sample solution injector 307. A chloride ion that is the target for measurement in the sample solution is bonded to the quaternary ammonium salt derivative 312 serving as the ligand for an anion by ion exchange action, so that the interface potential on the gold electrode 311 is changed. In the potential measurement, a current which flows between the source 309 and the drain 310 in the insulated gate field-effect transistor 304, and which is changed prior to and after the sample solution injection with the sample solution injector 307 is monitored in real time, and then recorded by use of the signal processing circuit 302 and the data processor 303. The interface potential change on the gold electrode 311 depends on the concentration of the chloride ion that is the target for measurement. Therefore, on the basis of a calibration curve constructed in advance by measuring standard solutions, an unknown chloride ion concentration of the sample can be obtained from the measured potential change value. The power source 306 is preferably a power source including an alternating current component to reduce the influence due to fluctuation outside the measurement. In that case, the stabilization of the surface potential of the gold electrode 311 can be expected by superimposing an alternating voltage of 1 KHz or more on a direct-current component.

The sample solution injector 307 can utilize a syringe pump or a pressurizing-type solution sending device. In addition, in place of the gold electrode 311, an electrode made of carbon or another noble metal such as silver may be used. Additionally, a high-molecular weight polymer may be physically adsorbed on the gold electrode and used to reduce an influence of adsorption of impurities on the electrode surface when a biological component is measured. The high-molecular weight polymer that may be used without problems includes methyl cellulose, acrylamide, dextran, polyethylene glycol, and the like.

The reference electrode 305 gives a reference potential in order to stably measure a potential change on the basis of an equilibration reaction or a chemical reaction taking place on the surface of the gold electrode 311 within the measurement solution 314. Normally, a calomel electrode or a silver/silver chloride electrode in which a saturated potassium chloride solution is used as an internal solution is used as the reference electrode. However, when the composition of a sample solution to be measured is uniform, only a silver/silver chloride electrode can be used as a pseudo-electrode without problems.

Figure 4A:
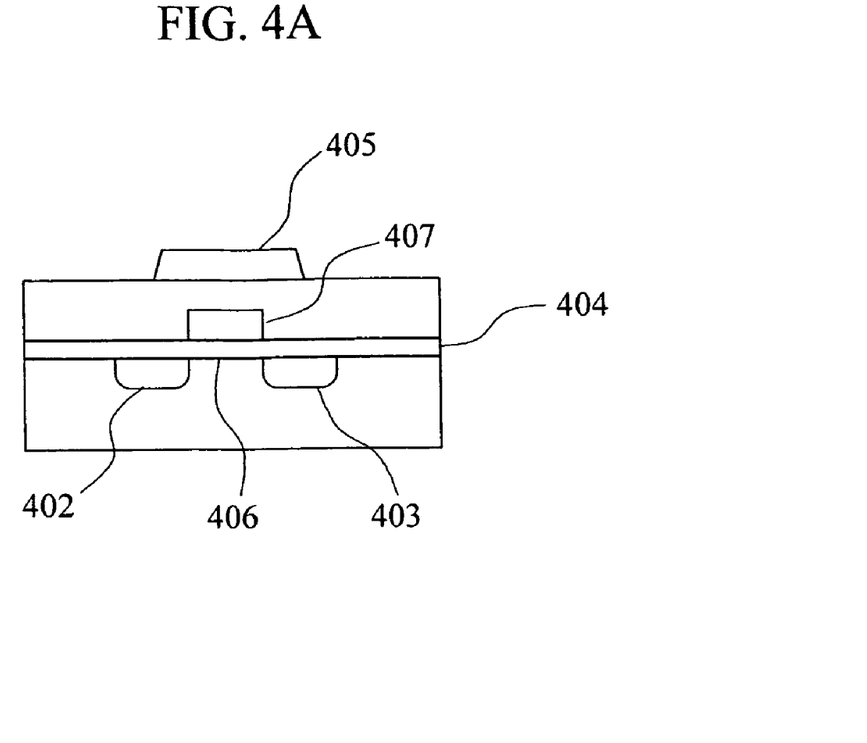
FIG. 4A is a sectional view thereof.
Figure 4B:
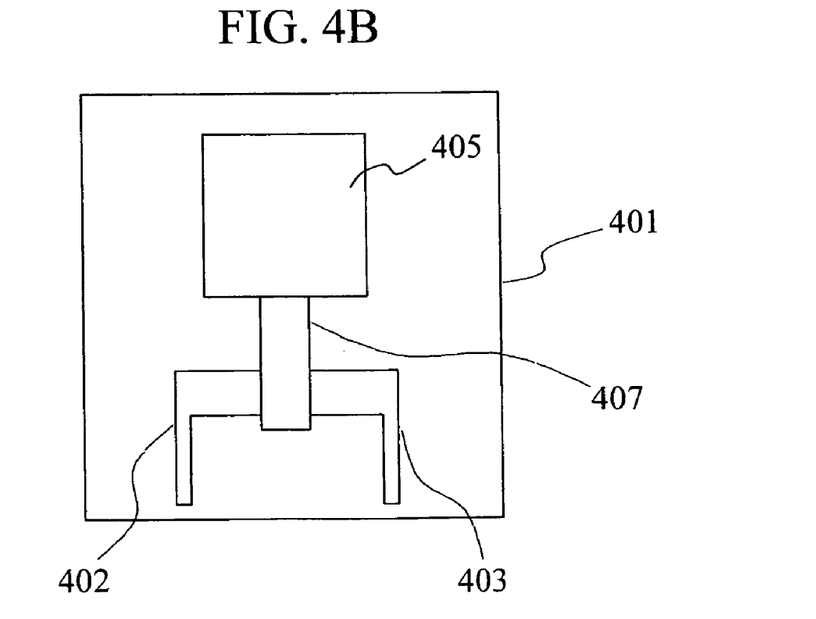
FIG. 4B is a plan view thereof.

FIG. 4 is a diagram indicating one example of a structure of an analysis element with an FET sensor used for the ion concentration measuring device of the present invention. FIGS. 4A and 4B show respectively sectional and planar structures. An insulated gate field-effect transistor 401 has a source 402, a drain 403 and a gate insulator 404 formed on its silicon substrate surface, and is provided with a gold electrode 405. The gold electrode 405 is connected to a gate 406 of the insulated gate field-effect transistor with a conductive wiring 407. Although the insulated gate field-effect transistor is preferably a metal-oxide semiconductor field-effect transistor (FET) using silicon oxide as an insulating film, a thin film transistor (TFT) can be used without problems. The adoption of this structure makes it possible to form the gold electrode 405 in an arbitrary place and in an arbitrary size, and to alter the volume of a measurement cell in accordance with the amount of sample solution that is a target for measurement.

The insulated gate field-effect transistor used in the present invention is a depletion type FET having an insulating layer using $SiO_2$ (thickness: 17.5 nm), and its gold electrode is fabricated in a size of 400 μm×400 μm. In normal measurement, an aqueous solution is used, so that the present element must be operated in the solution. When measurement is performed in the solution, the operation needs to be performed in the electrode potential range from −0.5 V to 0.5 V where an electrochemical reaction is difficult to occur. Thus, in this embodiment, the fabrication conditions of the depletion type n channel FET, that is, the ion implantation conditions for adjusting a threshold voltage (Vt) are adjusted, and the threshold voltage of FET is set to about −0.5 V. In addition, in place of the gold electrode, an electrode made of another noble metal such as silver may be used. An element having two or more FET sensors on the same substrate is fabricated by forming the multiple FET sensors of FIG. 4 on the same substrate. The problematic crosstalk between the FET sensors caused in that case can be decreased if an SOI (Silicon on Insulator) structure is adopted.

Next, described will be effects of causing an alkanethiol having an hydrophilic terminal, particularly having an amino group at the terminal to coexist with a quaternary ammonium salt derivative and immobilizing them when the quaternary ammonium salt derivative serving as a ligand for an anion is immobilized to the gold electrode surface with a linker that is an insulating molecule.

The immobilization of the ligand to the gold electrode surface was carried out in the following procedure. First, a gold electrode used in the immobilization was washed with 1 N nitric acid, purified water and ethanol in the order listed, and the gold electrode surface was purged with nitrogen. Then, the gold electrode was immersed for one hour in a mixture solution of a ligand and an alkanethiol (each concentration: 0.5 mM, solvent: ethanol). After completion of the immobilization, the gold electrode was kept in a 300 mM sodium chloride solution for 10 minutes at 95° C. Thereafter, the gold electrode was washed with ethanol and purified water, and stored in a 300 mM aqueous sodium chloride solution till its use.

The influence of the length of the carbon chain and the terminal residue of an alkanethiol on a response speed to a chloride ion will be described below; the alkanethiol is immobilized to the gold electrode surface to coexist with the quaternary ammonium salt derivative serving as the ligand for an anion.

In this embodiment, N,N,N-trimethyl(10-mercaptodecyl) ammonium chloride that is one example of the quaternary ammonium salt derivative in which 1-decanethiol served as the linker was used as the ligand for a chloride ion. 1-Octanethiol (1-OT), 1-undecanethiol (1-UDT), 1-tetradecanethiol (1-TDT) and 1-octadecanethiol (1-ODT) that are hydrophobic alkanethiols were used as an alkanethiol having a methyl group at the terminal. 6-Hydroxy-1-hexanethiol (6-HHT), 8-hydroxy-1-octanethiol (8-HOT), 11-hydroxy-1-undecanethiol (11-UUT), and triethylene glycol-mono-11-mercaptodecylether (TGM) that has hydrophilic ethylene glycol and a carbon chain length corresponding to 18 carbon atoms, were used as an alkanethiol having a hydroxyl group at the terminal. 6-Amino-1-hexanethiol (6-AHT), 8-amino-1-octanethiol (8-AOT), and 11-amino-1-undecanethiol (11-AUT) were used as an alkanethiol having an amino group at the terminal. The response speed to a chloride ion was measured as a time until the potential response to the ionic concentration was changed by 90%.

Figure 5A:
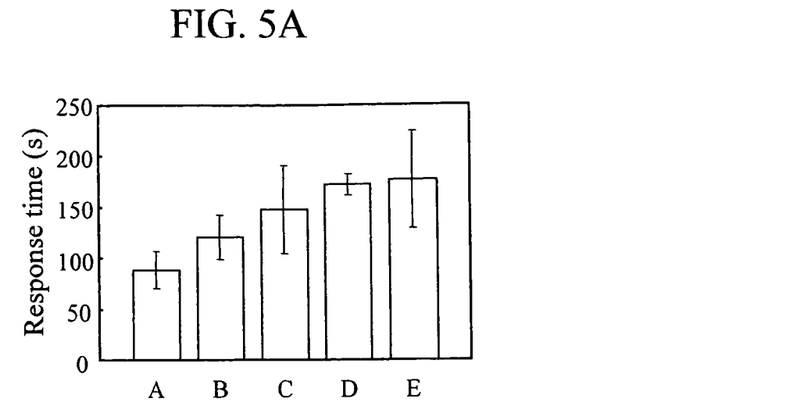
FIG. 5A is a diagram when a hydrophobic alkanethiol having a methyl group at its terminal is made to coexist.

FIG. 5A shows the influence of the length of the carbon chain on a response speed to a chloride ion when a ligand coexists with the alkanethiols each having a methyl group at the terminal in a ratio of 1:1. In the abscissa of FIG. 5A, A represents a gold electrode to which only a ligand is immobilized; B represents a gold electrode to which a ligand and 1-OT are immobilized; C represents a gold electrode to which a ligand and 1-UDT are immobilized; D represents a gold electrode to which a ligand and 1-TDT are immobilized; and E represents a gold electrode to which a ligand and 1-ODT are immobilized. FIG. 5A shows that the longer the length of the carbon chain of the coexisting alkanethiol is, the lower the response speeds of the chloride ion electrodes on which alkanethiols with a variety of carbon chain lengths are immobilized in a coexisting manner. This suggests that an adverse effect in which the response becomes slow due to an increase in hydrophobicity in peripheries of the ligand, is larger than an improved effect on the response in which the alkanethiol is simply buried in a space of interligands to prevent an ion from intruding into the space of interligands. In other words, it is shown that the increase in hydrophobicity in peripheries of the ligand makes a chloride ion hardly approach the ligand.

Figure 5B:
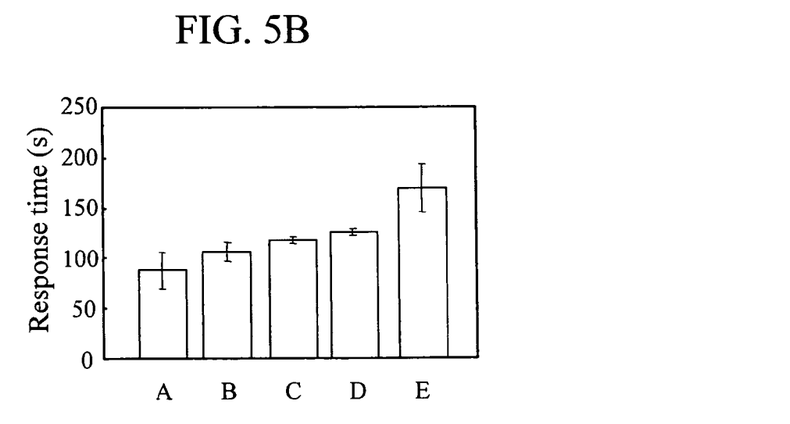
FIG. 5B is a diagram when a hydrophilic alkanethiol having a hydroxyl group at its terminal is made to coexist.

FIG. 5B shows the influence of the length of the carbon chain on a response speed to a chloride ion when a ligand coexists with the alkanethiols each having a hydroxyl group at the terminal in a ratio of 1:1. In the abscissa of FIG. 5B, A represents a gold electrode to which only a ligand is immobilized; B represents a gold electrode to which a ligand and 6-HHT are immobilized; C represents a gold electrode to which a ligand and 8-HOT are immobilized; D represents a gold electrode to which a ligand and 11-HUT are immobilized; and E represents a gold electrode to which a ligand and TGM are immobilized. FIG. 5B shows that the response speeds of the chloride ion electrodes on which the alkanethiols having the hydroxyl groups with the variety of carbon chain lengths at the terminals were immobilized to coexist with the ligand, become almost the same as the case where only a ligand is immobilized. In addition, in the case where TGM having hydrophilic ethylene glycol and a carbon chain length corresponding to 18 carbon atoms was immobilized to coexist with the ligand, the TGM exhibited almost the same response speed as that of 1-ODT of a hydrophobic alkanethiol having the same carbon chain length, and thus had a slow response. This shows that the effect of the steric hindrance is larger than the hydrophilic effect. Thus, it is considered that as the length of the carbon chain of an alkanetiol is too large, a chloride ion hardly approaches the ligand due to the steric hindrance around the ligand, and that the response speed becomes slow.

Figure 5C:
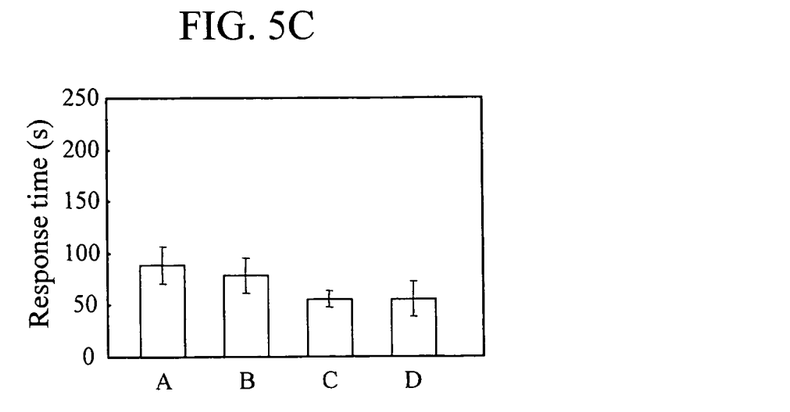
FIG. 5C is a diagram when a hydrophilic alkanethiol having an amino group at its terminal is made to coexist.

FIG. 5C shows the influence of the length of the carbon chain on a response speed to a chloride ion when a ligand coexists with the alkanethiols each having an amino group at the terminal in a ratio of 1:1. In the abscissa of FIG. 5C, A represents a gold electrode to which only a ligand is immobilized; B represents a gold electrode to which a ligand and 6-AHT are immobilized; C represents a gold electrode to which a ligand and 8-AOT are immobilized; and D represents a gold electrode to which a ligand and 11-AUT are immobilized. FIG. 5C shows that, as the length of the carbon chain of the coexisting alkanethiols increases, the response sensitivity to the chloride ion electrode on which the alkanethiols having the variety of carbon chain lengths are made to be immobilized and to coexist, becomes large in comparison with the case of the gold electrode to which only a ligand is immobilized. This seems to be because an alkanethiol buries a space of interligands to thereby prevent an ion from intruding the space.

FIGS. 5A to 5C show that the introduction of a hydrophilic group, particularly an amino group, to an alkanethiol that coexists with a ligand improves the response speed to a chloride ion. In other words, it is better that an alkanethiol that is made to coexist with a ligand for a chloride ion is hydrophilic, and that the length of the carbon chain is shorter than that of the ligand. In particular, it is desired that the length of the alkanethiol be equal to or shorter than the length of the coexisting ligand, and that the alkanethiol have an amino group.

Hereinbelow, described will be the results of measured potential responses to chloride ions by use of an ion-selective electrode of the present invention in which a quaternary ammonium salt derivative serving as a ligand for an anion and an alkanethiol having an amino group at its terminal are immobilized to the surface of a gold electrode with a linker that is an insulating molecule, to coexist with each other.

Figure 6:
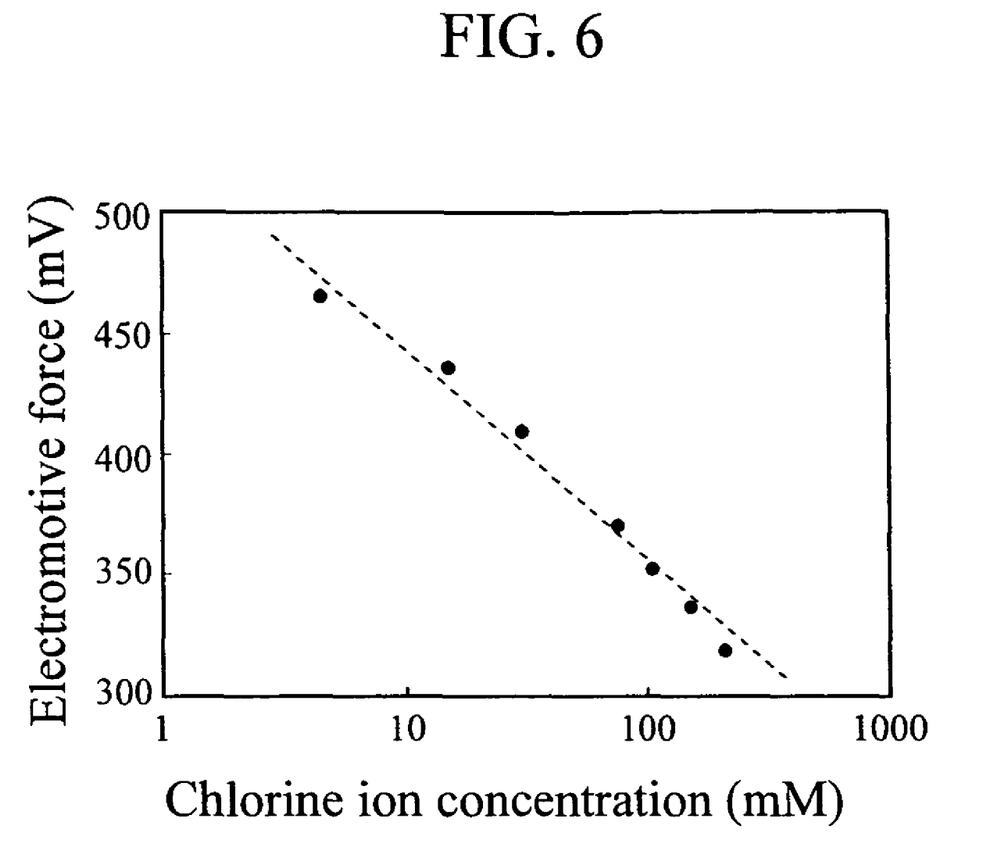
FIG. 6 is a diagram indicating a result obtained by measuring a chloride ion concentration using an ion-selective electrode in which an alkanethiol having an amino group at its terminal and a quaternary ammonium salt derivative as a ligand are made to coexist.

In this embodiment, N,N,N-trimethyl(10-mercaptodecyl) ammonium chloride that is one example of the quaternary ammonium salt derivative in which 1-decanethiol served as the linker was used as the ligand for a chloride ion. 11-Amino-1-undecanethiol (11-AUT) was used as an alkanethiol having an amino group at the terminal. The potential response to a chloride ion was measured using an aqueous sodium chloride solution, and slope sensitivities were compared in the concentration range from 4.5 mM to 300 mM (FIG. 6). In addition, the potential measurement value is a value obtained five minutes after the immersion. The abscissa of FIG. 6 represents a chloride ion concentration in terms of the activity. The ordinate shows an electromotive force generated according to the number of chloride ions. As a result, the potential response to a chloride ion followed Nernst's equation, and the slope sensitivity was about 60 mV.

Figure 7:
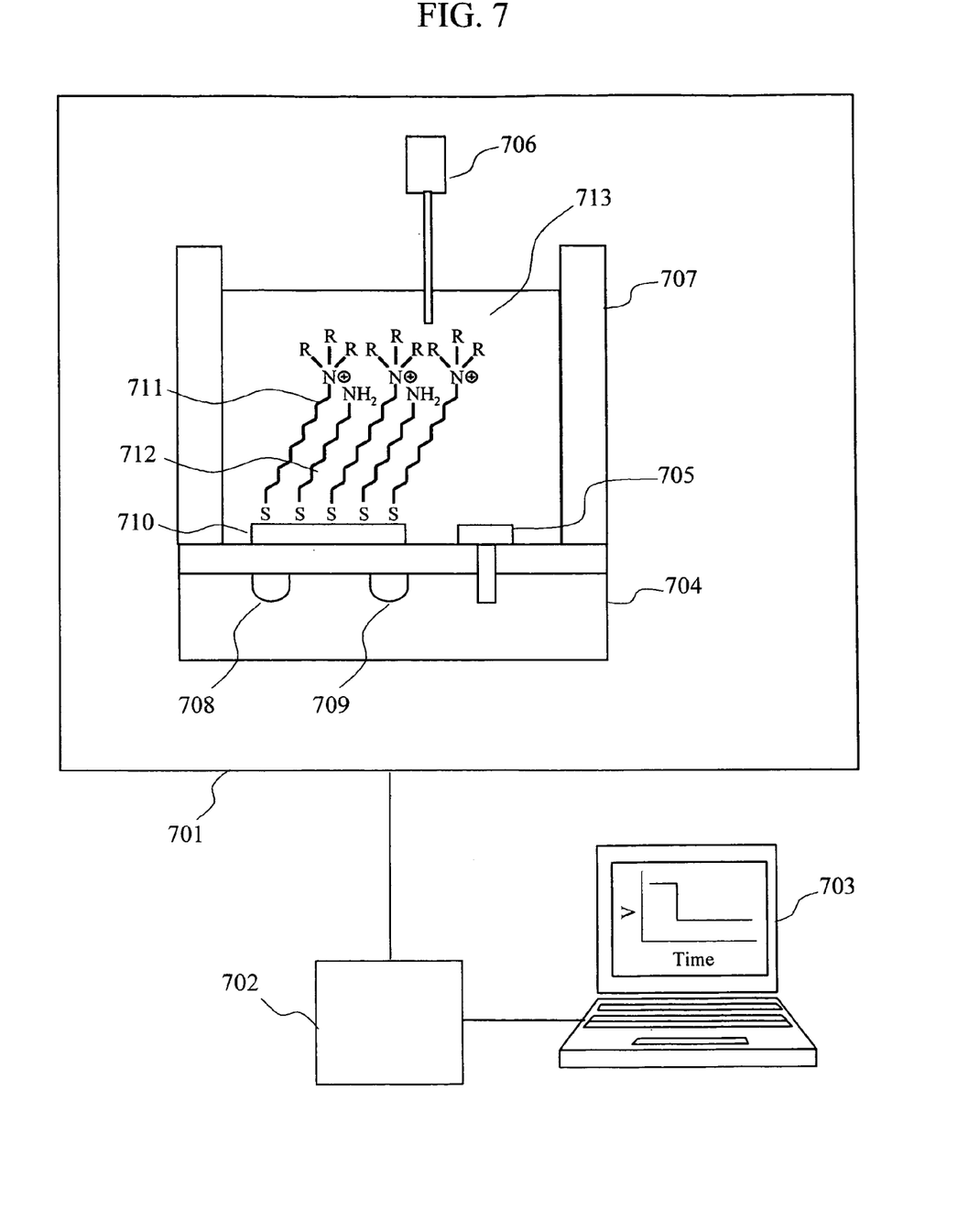
FIG. 7 is a block diagram indicating one example of an ion concentration measuring device of the present invention in which an FET sensor and a reference electrode are formed in the same plane.

FIG. 7 is a block diagram indicating one example of an ion concentration measuring device of the present invention in which an FET sensor and a reference electrode are formed in the same plane. The measuring device of this embodiment includes a measurement section 701, a signal processing circuit 702, and a data processor 703. The measurement part 701 includes an insulated gate field-effect transistor 704, a pseudo-reference electrode 705, a sample solution injector 706 that supplies a sample solution having an analyte, and a measurement cell 707. The insulated gate field-effect transistor 704 includes a source 708, a drain 709 and a gold electrode 710 electrically connected to a gate. In addition, the pseudo-reference electrode 705 is disposed on the same plane as the gold electrode 710. The pseudo-reference electrode 705 is connected to the outside via a conductivity wiring. As the pseudo-reference electrode, silver/silver chloride, gold, platinum or the like can be used. In this embodiment, a quaternary ammonium salt derivative 711 serving as a ligand for a chloride ion and an alkanethiol 712 having an amino group at its terminal are immobilized to the gold electrode 710. The pseudo-reference electrode 705 and the gold electrode 710 on which the quaternary ammonium salt derivative 711 serving as the ligand for a chloride ion and the alkanethiol 712 having an amino group at its terminal are immobilized, are arranged in a measurement solution 713 within the measurement cell 707. An alternating voltage of 1 kHz or more is superimposed on a direct-current component, and then applied to the pseudo-reference electrode 705.

Figure 8A:
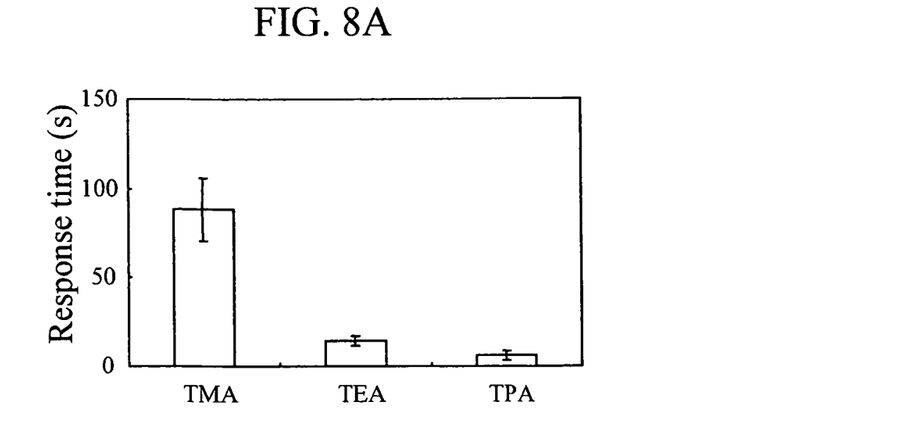
FIG. 8 is a diagram indicating influences of the length of a side chain of a quaternary ammonium salt used as a ligand of a chloride ion-selective electrode, on a response speed to a chloride ion concentration.
Figure 8B:
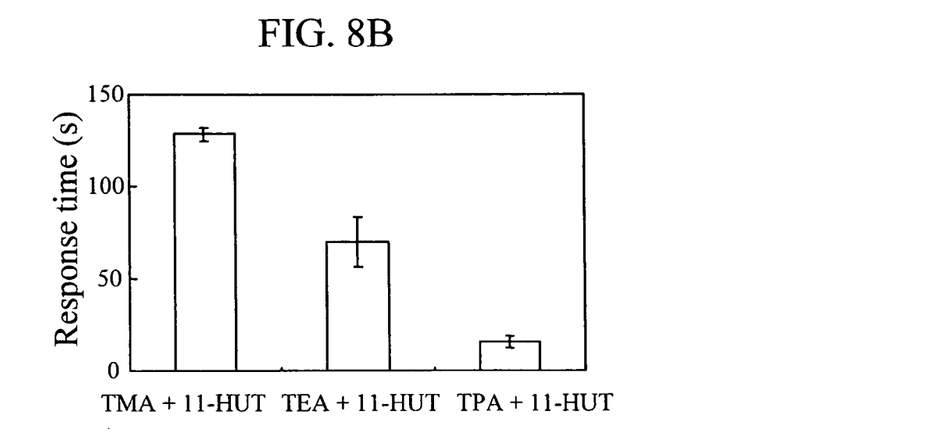

FIG. 8 indicates the influence of the length of a side chain of a quaternary ammonium salt used as a ligand of a chloride ion-selective electrode, on a response time to a chloride ion concentration. In this embodiment, as showed in FIGS. 9A, 9B and 9C, N,N,N-trimethyl(10-mercaptodecyl)ammonium chloride having a methyl group as its side chain, N,N,N-triethyl(10-mercaptodecyl)ammonium chloride having an ethyl group as its side chain, and N,N,N-tripropyl(10-mercaptodecyl)ammonium chloride having a propyl group as its side chain were used as examples of the quaternary ammonium salt. This embodiment shows the influences of the side chains of the quaternary ammonium salts serving as the ligands in a case where a ligand and a hydrophilic alkanethiol are made to coexist, in addition to a case where only a ligand is immobilized, and the influences are compared. TMA, TEA, TPA, 11-HUT and 11-AUT in the drawing indicate N,N,N-trimethyl(10-mercaptodecyl)ammonium chloride, N,N,N-triethyl(10-mercaptodecyl)ammonium chloride, N,N,N-tripropyl(10-mercaptodecyl)ammonium chloride that is a propyl group, 11-hydroxy-1-undecanethiol, and 11-amino-1-undecanethiol, respectively.

Figure 8C:
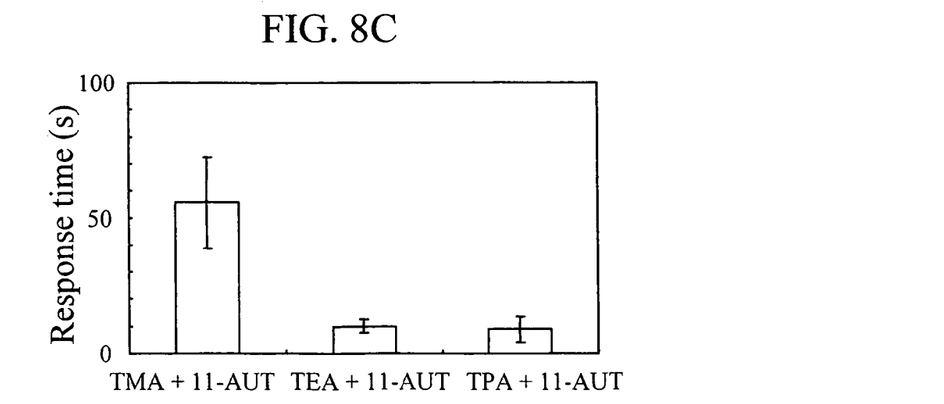
Figure 9A:
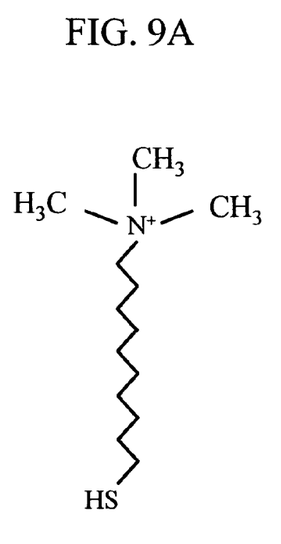
FIG. 9 is a diagram indicating one example of a quaternary ammonium salt serving as a ligand for a chloride ion.
Figure 9B:
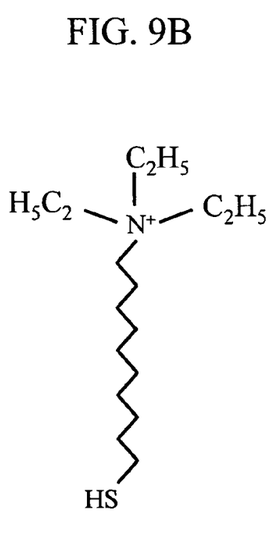
Figure 9C:
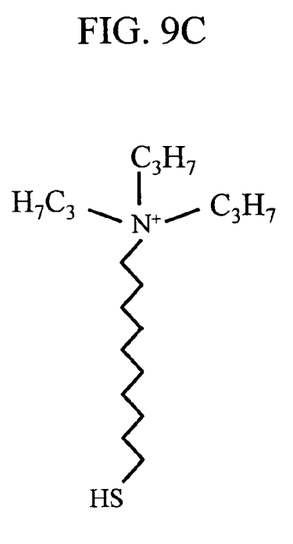

As a result, in both cases where only a ligand was immobilized and where a ligand was made to coexist with a hydrophilic alkanethiol, the response time was remarkably shortened, as the carbon chain of the side chain of the quaternary ammonium salt was lengthened. In this embodiment, in the case where only a ligand is immobilized, the response time was: 88 second when the side chain was a methyl group; 14 second when the side chain was an ethyl group; and 6 second where the side chain was a propyl group. In addition, when the side chain was a methyl group, as shown in FIG. 8C, the response time in the case where a ligand is made to coexist with an alkanethiol having an amino group is faster than that of the case of only a ligand. However, the effect became small as the length of the side chain of the quaternary ammonium salt increased. When the side chain was a propyl group, the response time was the shortest in the case where only a ligand was immobilized.

In this manner, by making long the side chain of a quaternary ammonium salt, the salt can be immobilized to a gold electrode using a simple composition therefor and without requiring another hydrophilic alkanethiol. In that case, the number of carbon atoms of an alkyl group at a side chain of a quaternary ammonium salt derivative is desirably smaller than the number of carbon atoms of a linker so as not to hinder self assembly at the time of immobilization of the quaternary ammonium salt to the gold electrode. For instance, in this embodiment, the length of the carbon chain of the linker has 10 carbon atoms, and thus the number of carbon atoms at the side chain is desirably 10 or smaller. In addition, the carbon chain of the linker of the quaternary ammonium salt derivative that is the ligand for a chloride ion can be changed according to measurement conditions. However, the number of carbon atoms is desirably 20 or less, in consideration of a chemical synthetic technique, a refining method after synthesis and an immobilization method to a gold electrode.

Figure 10A:
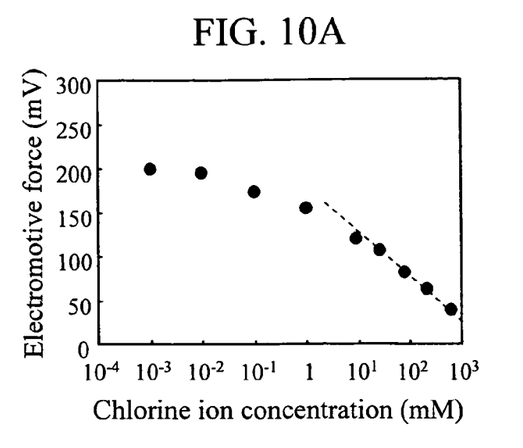
FIG. 10 is a diagram indicating the relationship between the length of the side chain of a quaternary ammonium salt derivative serving as a ligand of a chloride ion-selective electrode and an electric potential response to a chloride ion concentration.
Figure 10B:
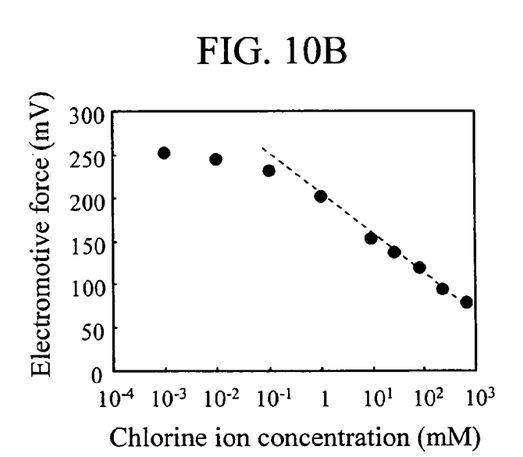
Figure 10C:
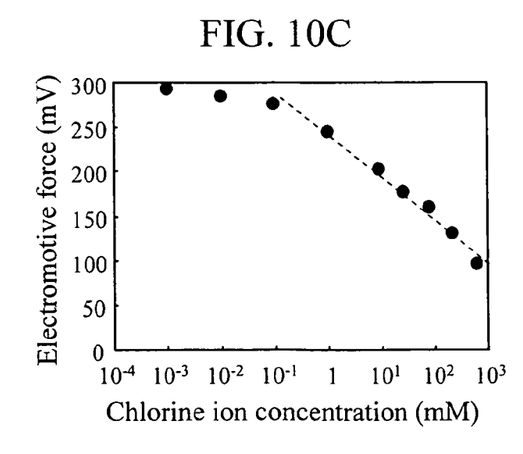

FIG. 10 indicates the relationship between the length of the side chain of a quaternary ammonium salt derivative serving as a ligand and a potential response to a chloride ion concentration. In this embodiment, as examples of the quaternary ammonium salt, the substances indicated in FIGS. 9A, 9B, and 9C were used. FIG. 10A indicates a case where N,N,N- trimethyl(10-mercaptodecyl)ammonium chloride having a methyl group as a side chain was used. FIG. 10B indicates a case where N,N,N-triethyl(10-mercaptodecyl)ammonium chloride having an ethyl group as a side chain was used. FIG. 10C indicates a case where N,N,N-tripropyl(10-mercaptodecyl)ammonium chloride having a propyl group as a side chain was used. The potential responses to the concentration of a chloride ion were measured using an aqueous sodium chloride solution, and the electromotive forces on the surfaces of ligand immobilization electrodes in the concentration range from 0.001 mM to 1000 mM were compared.

The abscissa of FIG. 10 shows the concentration of a chloride ion in terms of the activity. The ordinate shows the electromotive force generated responding to a chloride ion. When the length of the side chain of the quaternary ammonium salt was increased, the potential response to the concentration of a chloride ion was found even at a lower concentration. In this embodiment, the linearity can be maintained in the concentration range from 10 mM to 1000 mM when the side chain is a methyl group, from 1 mM to 1000 mM when the side chain is an ethyl group, and from 0.1 mM to 1000 mM when the side chain is a propyl group. In other words, it is shown that the longer the side chain of the quaternary ammonium salt, the shorter the response time, and also that the wider the range indicating a linear response (measurement range).

Figure 11:
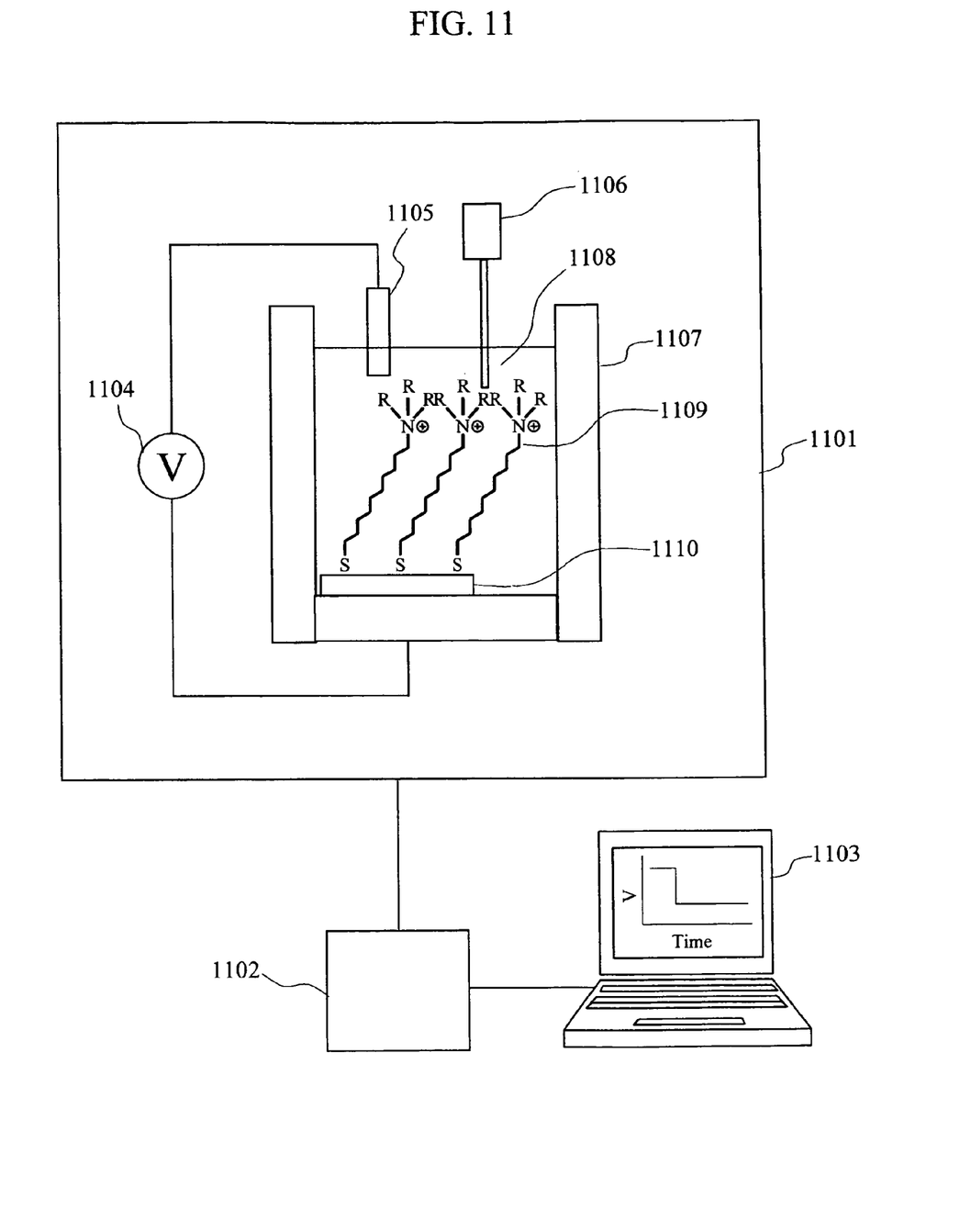
FIG. 11 is a block diagram indicating one example of an ion concentration measuring device according to the present invention.

FIG. 11 is a block diagram indicating one example of an ion concentration measuring device according to the present invention. The measuring device of this embodiment includes a measurement section 1101, a signal processing circuit 1102 and a data processor 1103. The Measurement section 1101 includes a potentiometer 1104, a reference electrode 1105, a sample solution injector 1106 that supplies a sample solution having an analyte, and a measurement cell 1107. The reference electrode 1105 and a gold electrode 1110 to which a quaternary ammonium salt derivative 1109 serving as a ligand for an anion is immobilized, are arranged in a measurement solution 1108 within the measurement cell 1107. In this embodiment, because of use of N,N,N-tripropyl(10-mercaptodecyl)ammonium chloride as the ligand for a chloride ion, a high response speed can be obtained even if a hydrophilic alkanethiol is not immobilized in a coexisting manner. In addition, the carbon chain of an alkyl group at a side chain of the quaternary ammonium salt derivative serving as the ligand for a chloride ion can be altered according to measurement conditions. In that case, the number of carbon atoms of the alkyl group at the side chain of the quaternary ammonium salt derivative is desirably smaller than the number of carbons of a linker so as not to prevent self assembly when the ligand is immobilized to the gold electrode. For example, in this embodiment, since the number of carbon atoms of the carbon chain of the linker is 10, the number of carbon atoms of the carbon chain is desirably 10 or smaller.

Explanation of Reference Numerals 101, 301, 701, 1101 . . . Measurement section
102, 302, 702, 1102 . . . Signal processing circuit
103, 303, 703, 1103 . . . Data processor
104, 1104 . . . Potentiometer
105, 305, 1105 . . . Reference electrode
106, 307, 706, 1106 . . . Sample solution injector that supplies a sample solution having an analyte
107, 308, 707, 1107 . . . Measurement cell
108, 314, 713, 1108 . . . Measurement solution
109, 312, 711, 1109 . . . Quaternary ammonium salt derivative serving as a ligand for an anion
110, 313, 712 . . . Alkanethiol having an amino group at its terminal
111, 311, 405, 710, 1110 . . . Gold electrode
304, 401, 704 . . . Insulated gate field-effect transistor
306 . . . Power source
309, 402, 708 . . . Source
310, 403, 709 . . . Drain
404 . . . Gate insulator
406 . . . Gate of an insulated gate field-effect transistor
407 . . . Conductivity wiring
705 . . . Pseudo-reference electrode

What is claimed is:

1. An anion concentration measuring device, comprising:
   a container into which a measurement solution containing a target material for measurement is introduced;
   an ion-selective electrode in contact with the measurement solution in the container;
   a reference electrode in contact with the measurement solution in the container; and
   a potentiometer which measures an interface potential of the ion-selective electrode, wherein
   a quaternary ammonium salt is immobilized to the ion-selective electrode,
   one side chain of the quaternary ammonium salt is an alkanethiol group immobilized to the ion-selective electrode via a thiol bond between the alkanethiol group and the ion-selective electrode, and
   the other three side chains are alkyl chains.

2. The anion concentration measuring device according to claim 1, wherein
   the number of carbon atoms of the alkyl chain at each of the other three side chains of the quaternary ammonium salt is from 1 to 20 inclusive.

3. The anion concentration measuring device according to claim 1, wherein
   an alkanethiol including one hydrophilic terminal is immobilized to the ion-selective electrode to coexist with the quaternary ammonium salt.

4. The anion concentration measuring device according to claim 3, wherein
   a hydrophilic group of the hydrophilic terminal of the alkanethiol coexisting with the quaternary ammonium salt is any one of an amino group and a hydroxyl group.

5. The anion concentration measuring device according to claim 3, wherein
   the carbon chain of the alkanethiol coexisting with the quaternary ammonium salt is shorter than the carbon chain of the alkanethiol that is the one side chain of the quaternary ammonium salt.

* * * * *